United States Patent
Paton et al.

(10) Patent No.: US 9,936,622 B2
(45) Date of Patent: Apr. 10, 2018

(54) APPARATUS FOR APPLYING A PESTICIDE TO PERENNIAL CROPS

(71) Applicant: Sumitomo Chemical Company, Limited, Tokyo (JP)

(72) Inventors: Douglas Paton, Chatswood (AU); David Smith, Chatswood (AU)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 91 days.

(21) Appl. No.: 14/464,496

(22) Filed: Aug. 20, 2014

(65) Prior Publication Data
US 2014/0352585 A1 Dec. 4, 2014

Related U.S. Application Data

(62) Division of application No. 12/743,331, filed as application No. PCT/AU2008/001746 on Nov. 26, 2008, now Pat. No. 8,844,451.

(30) Foreign Application Priority Data

Nov. 29, 2007 (AU) ................................ 2007906522

(51) Int. Cl.
*A01B 35/32* (2006.01)
*A01B 39/16* (2006.01)
(Continued)

(52) U.S. Cl.
CPC .............. *A01B 49/06* (2013.01); *A01B 35/32* (2013.01); *A01B 39/16* (2013.01); *A01B 63/004* (2013.01);
(Continued)

(58) Field of Classification Search
CPC ......... A01B 35/32; A01B 35/00; A01B 39/16; A01B 39/12; A01B 39/00; A01B 63/004;
(Continued)

(56) References Cited

U.S. PATENT DOCUMENTS 3,319,589 A 5/1967 Morgan et al.
3,683,547 A 8/1972 Harden
(Continued)

FOREIGN PATENT DOCUMENTS

| JP | 2005-185203 A | 7/2005 |
|---|---|---|
| JP | 2007-259781 A | 10/2007 |
| WO | WO 2009/067739 A1 | 6/2009 |

OTHER PUBLICATIONS

The Office Action (including an English translation), dated Feb. 12, 2015, issued in the corresponding Korean Patent Application No. 2010-7011551.
(Continued)

*Primary Examiner* — Christopher J. Novosad
(74) *Attorney, Agent, or Firm* — Birch, Stewart, Kolasch & Birch, LLP

(57) ABSTRACT

An applicator assembly for applying an active substance to the root zone of a plurality of plants, the applicator assembly comprising: a subsoil applicator having a cutting element for generating an incision in the ground, an injector associated with the cutting element to allow the active substance to be injected into the incision; and a positioning device adapted to allow the position of the cutting element to change position such that an incision is generated in some material in the root zone while the cutting element moves over other material in the root zone.

17 Claims, 6 Drawing Sheets

(51) Int. Cl.

| | |
|---|---|
| *A01B 63/00* | (2006.01) |
| *A01B 49/06* | (2006.01) |
| *A01C 21/00* | (2006.01) |
| *A01C 23/02* | (2006.01) |
| *A01G 29/00* | (2006.01) |
| *A01N 25/00* | (2006.01) |

(52) U.S. Cl.
CPC ............ *A01C 21/00* (2013.01); *A01C 21/002* (2013.01); *A01C 23/025* (2013.01); *A01G 29/00* (2013.01); *A01N 25/00* (2013.01); *Y02A 40/243* (2018.01); *Y02P 60/40* (2015.11)

(58) Field of Classification Search
CPC ....... A01B 63/002; A01B 63/00; A01B 49/06; A01B 49/04; A01B 49/00; A01C 21/00; A01C 21/002; A01C 23/025; A01C 23/023; A01C 23/02; A01C 23/00; A01G 29/00; A01N 25/00; Y02P 60/40; Y02P 60/00
See application file for complete search history.

(56) References Cited

U.S. PATENT DOCUMENTS

| | | | |
|---|---|---|---|
| 3,799,079 | A | 3/1974 | Dietrich |
| 5,279,068 | A | 1/1994 | Rees et al. |
| 5,520,125 | A | 5/1996 | Thompson et al. |
| 5,558,471 | A | 9/1996 | Payne |
| 5,727,484 | A * | 3/1998 | Childs .................. A01C 23/026 111/7.1 |
| 6,505,568 | B1 | 1/2003 | Miers |
| 6,901,720 | B2 | 6/2005 | Lechner et al. |
| 7,004,090 | B2 | 2/2006 | Swanson |
| 2003/0005866 | A1 | 1/2003 | Miers |
| 2005/0098713 | A1 | 5/2005 | Holland |
| 2005/0197252 | A1 * | 9/2005 | Yamashita .............. C05F 11/00 504/103 |
| 2007/0113762 | A1 | 5/2007 | Phillips, Jr. |

OTHER PUBLICATIONS

An Office Action issued in the corresponding Canadian Patent Application No. 2,705,760 on Jul. 13, 2015.
Notice of Final Rejection (including an English translation) issued in the corresponding Korean Patent Application No. 2010-7011551 dated Aug. 31, 2015.
The Patent Examination Report No. 1, dated Jun. 13, 2014, issued in the corresponding Australian Patent Application No. 2008329545.
The Examination Report, dated Oct. 30, 2014, issued in the corresponding Canadian Patent Application No. 2,705,760.
Chinese Office Action dated Mar. 5, 2012, for Application No. 200880117624.4 with the English translation.
Office Action for corresponding Colombian Patent Application No. 10-061 658, dated Oct. 16, 2012.
Partial English-Language Translation for Office Action issued in corresponding Colombian Patent Application No. 10-061 658, dated Oct. 16, 2012.
The Notification of Reasons for Refusal, dated Sep. 10, 2013, issued in corresponding Japanese Patent Application No. 2010-535173.
The Substantive Examination Adverse Report and Search Report, dated Oct. 14, 2013, issued in corresponding Malaysian Patent Application No. PI 2010001982.
The extended European Search Report, dated Feb. 19, 2015, issued in the corresponding European Patent Application No. 08855003.3.
First Examination Report issued in the corresponding Indian Patent Application No. 2866/CHENP/2010 dated Jan. 16, 2017.
European Patent Office Communication pursuant to Article 94(3) EPC issued in the corresponding European Patent Application No. 08855003.3 dated Dec. 15, 2016.
Brazilian Office Action and Search Report, published in the Brazilian Gazette dated Feb. 14, 2017, for Brazilian Application No. PI0819762-8, with an English translation of the Brazilian Office Action.
Brazilian Gazette dated Aug. 8, 2017, informing that the rejection decision was drafted on Jun. 1, 2017 in the corresponding Brazilian Patent Application No. PI 0819762-8 (including a partial English translation thereof).

* cited by examiner

APPARATUS FOR APPLYING A PESTICIDE TO PERENNIAL CROPS

CROSS-REFERENCE TO RELATED APPLICATIONS

This application is a Divisional of co-pending application Ser. No. 12/743,331 filed on Oct. 5, 2010, which is a National Phase of PCT International Application No. PCT/AU2008/001746 filed on Nov. 26, 2008, which claims priority under 35 U.S.C. § 119(a) to Patent Application No. 2007906522 filed in Australia on Nov. 29, 2007. All of the above applications are hereby expressly incorporated by reference into the present application.

FIELD OF THE INVENTION

The invention relates to the horticultural and forestry fields. In particular, the invention relates to an apparatus for applying an active substance to perennial plants and to methods of applying active substances to perennial plants.

BACKGROUND ART

Many perennial plants are grown for commercial purposes. Perennial plants grown for commercial purposes (referred to herein as "perennial crops") include many fruit trees, such as apple trees, pear trees and citrus plants, fruit producing vines, such as grape vines, and trees grown for paper, pulp, wood chip or timber production. They can include temperate, sub tropical and tropical species.

Perennial crops are typically grown over large areas, e.g. in orchards or vineyards for fruit production or in forestry plantations for paper, pulp, wood chip or timber production.

Perennial crops can be affected by a variety of pests, including insects and fungi, which can reduce the growth or fruit production of the perennial crop and can result in damage or even death to the plants.

Various methods have been used to apply pesticides to perennial crops. One common method of applying pesticides to perennial crops is aerial spraying.

Insecticides such as neonicotinoids are absorbed systemically by plants through the plants root system. Similarly, fertiliser and plant food elements may be absorbed by the plant root system. Such absorption of insecticides, plant fertilizer or plant food or other compositions is effective in improving the growth of perennial plants.

Pesticides, insecticides, fertilizers and plant food have been applied to individual trees by injection into the soil at multiple locations around the tree or by injection directly into the tree. They also have been applied to seedlings as a pill deposited in the soil at the time of planting the seedlings. Further, they may be applied to citrus and apple trees as a drench on the soil surface around the tree.

These methods of application have a number of disadvantages for application to perennial crops or other perennial plants which are grown over a large area. The injection of a pesticide into the soil around each plant to be treated or injection of a pesticide or fertiliser into the plant is time consuming and labour intensive and therefore is an expensive method of applying a composition to perennial crops over large areas. Applying a drench to each plant can also be time consuming and can have adverse environmental effects as the drench may readily move from the site of application and be for example washed into waterways. The deposit of a pill in the soil at the time of planting a seeding is also time consuming and is not a method applicable for established plants. These methods of application also only allow for application at a slow speed and do not allow for easy application in heavily vegetated ground cover situations.

SUMMARY OF THE INVENTION

In a first aspect the present invention provides an applicator assembly for applying an active substance to the root zone of a plurality of plants, the applicator assembly comprising: a subsoil applicator having a cutting element for generating an incision in the ground, an injector associated with the cutting element to allow the active substance to be injected into the incision; and a positioning device adapted to allow the position of the cutting element to change position such that an incision is generated in some material in the root zone while the cutting element moves over other material in the root zone.

In one form the positioning device allows the cutting element to be positioned such that it can generate an incision in softer materials such as soil and slender roots while moving over hard materials such as rocks and thick roots.

In one form the positioning device is in the form of suspension that operates to resiliently bias the cutting element with respect to the ground.

In one form the applicator assembly further comprises a coupling to connect the applicator assembly with a vehicle. In one form, the coupling forms part of the positioning device and is resiliently biased toward the ground. In one form the coupling allows movement both vertically and laterally to the direction of movement 80 of the vehicle.

It can be seen that this applicator assembly allows for the application of an active substance to the root zone of plurality of plants by creating an incision in the root zone of the plants without destroying the plants. The applicator assembly applies this active substance to the subsoil region by generating the incision in soft material such as soil and slender roots while the cutting element is allowed to move over harder material such as rocks and thick roots. This allows the user to quickly create an incision for application of an active substance without destroying the plants. It allows for application at higher speeds and in more heavily vegetated ground cover areas because the applicator assembly cuts through the vegetation without fouling.

In one form the cutting element rotates about an axis, the rotation of the cutting element generating the incision. In one form the cutting element is a disk. In another form the cutting element is a spur.

In one form the applicator assembly further comprising a surface applicator positioned to apply an active substance to the ground surface. This allows for the simultaneous subsoil application of an active substance to the root zone and application of an active substance to the ground surface or foliage of the plant. The surface applicator may be attached to the same reservoir as the injector. Alternatively the surface applicator may be connected with a separate reservoir. Thus the active substance and the composition applied to the ground surface may be the same substance or may be different from one another.

In one form the surface applicator comprises a spray nozzle. In another form the surface applicator comprises a granule dispenser. In another form the surface applicator comprises both a spray nozzle and a granule dispenser.

In one form the active substance applied by the surface applicator is the same as the active substance applied by the subsoil applicator.

In one form the active substance applied by the surface applicator is different from the active substance applied by the subsoil applicator. For example, the active substance applied by the surface applicator cold be a herbicide, while the active substance applied by the subsoil applicator could be a fertiliser.

In one form the applicator assembly further comprises a deflector adapted to push low branches from the path of the surface applicator to allow the active substance to be applied to the base of the stem.

In one form the deflector comprises an elongate member having a leading edge and a trailing edge with respect to the direction of motion of the vehicle, the elongate member being oriented such that the leading edge is positioned closer to the vehicle than the trailing edge.

In one form the surface applicator is located on the deflector.

In one form the applicator assembly is adapted to deliver the active substance sufficiently proximal to each of the plurality of plants for the composition to be taken up by the roots of the plant.

In one form the applicator assembly is adapted to deliver the active substance at a soil depth of 2-30 cm.

In one form the injector is adapted to deliver a continuous application of active substance. In another form the injector is adapted to deliver discrete deposits of active substance.

In one form the applicator assembly further comprises a sensor adapted to sense the distance of a plant from the applicator assembly and apply active substance at a specific distance from the plant.

In one form the applicator assembly is used in applying the active substance over large areas and is arranged to operate at an average speed of over 4 km/hr.

In one form the plurality of plants is positioned in a row.

In a second aspect, the present invention provides an applicator assembly for applying a composition to the root zone of a plurality of plants. The applicator assembly comprises a cutting element for generating an incision in the ground, an injector associated with the cutting element to allow the active substance to be injected into the incision and a spray nozzle or granule applicator positioned to apply a composition onto the ground surface. It can be seen that this allows simultaneous application of an active substance to the root zone and a composition to the ground surface.

In a third aspect of the present is directed to a method of treating a plurality of plants, the method comprising generating an incision in a portion of the root zone of at least some of the plurality of plants; and injecting an active substance into the incision.

In one form the plants that are treated are in heavy terrain such as that found in forest plantations. In one form the method of treatment is performed by a vehicle mounted applicator assembly that travels at average speeds of over 4 km/hr.

In one form the portion of the root zone of a single plant in which the incision is generated extends from the plant at an angle of less than 180°. It can be seen that this allows an active substance to be delivered to the root zone without destroying all of the roots of the plant.

In one form the incision extends through some materials but moves over other materials.

In one form the incision is generated by a cutting element and the injection is performed by an injector associated with the cutting element. The cutting element and injector are positioned on a single applicator assembly.

In one form the method further comprises applying a liquid or applying a granule composition onto the surface of the ground proximal to each of the plurality of plants.

The inventors have found that the method and apparatus of at least one form disclosed has many advantages over other apparatus' and methods of applying an active substance to a plurality of plants. The subsurface application of the active substance means there is little volatilisation, run off or photo-degradation of the active substance. Further, the subsurface application of the active substance typically reduces the exposure of operators, workers, livestock and other organisms to the active substance, compared with aerial spraying or surface application of the active substance. These apparatus and method assist in the active substance being applied in a position where it is readily able to be taken up by the roots of the plants, which accelerate efficacy compared to other methods of applying active substances.

Further, the inventors have surprisingly found that the apparatus and method of at least one form disclosed is effective when used on a row of perennial plants even though the active substance is not applied uniformly around each plant. The application of an active substance below the soil surface near an established perennial plant has the disadvantage of disturbing the root system of the plant. The disturbance of the root system can have negative effects on the growth or fruit production of the plant. However, the application of an active substance below the soil surface in a line or series of deposits adjacent to the row of perennial plants only disturbs part of the root system of each plant. By applying the active substance below the soil surface in a line or series of deposits adjacent to the row of perennial plants, the active substance can be efficiently and cost-effectively applied to the perennial plants in the row. Thus the apparatus and method can be used to treat perennial plants where it would not be practical or economic to treat each plant individually by injecting the active substance into the plant or injecting the active substance into the soil in multiple locations around each plant.

The efficiency of application of the active substance is greatly increased by the applicator assembly which allows application in heavy terrain over wide areas at relatively high speeds without requiring regular breaks to clear an applicator assembly, clear the ground or circle the tree. Further the applicator assembly does not require second application of a further substance.

BRIEF DESCRIPTION OF THE DRAWINGS

Preferred embodiments will now be described, by way of example only, with reference to the accompanying drawings in which.

DETAILED DESCRIPTION OF THE INVENTION

Figure 1:
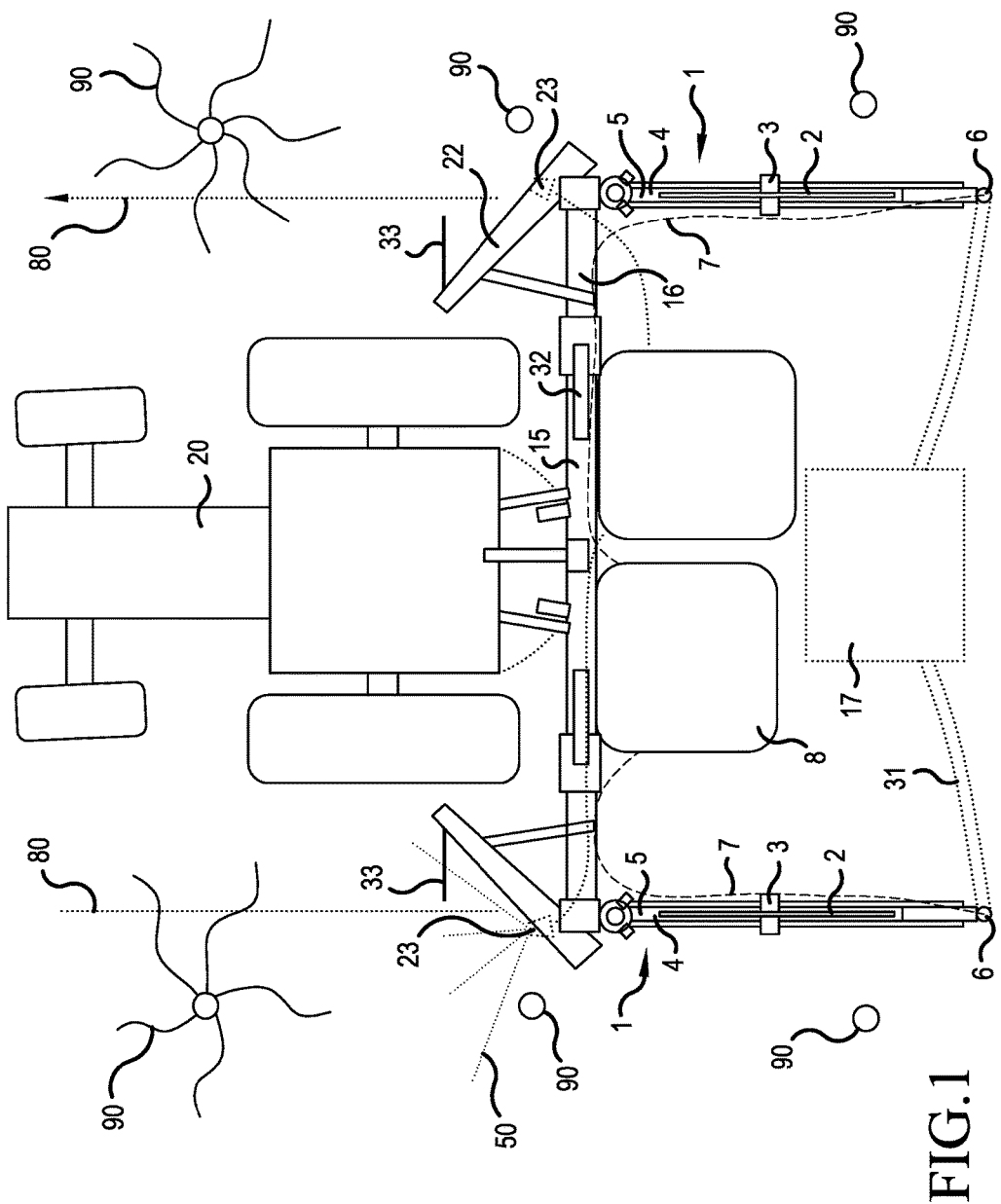
FIG. 1 is a top plan view of an applicator assembly in use on a vehicle in accordance with one embodiment of the invention.
Figure 2:
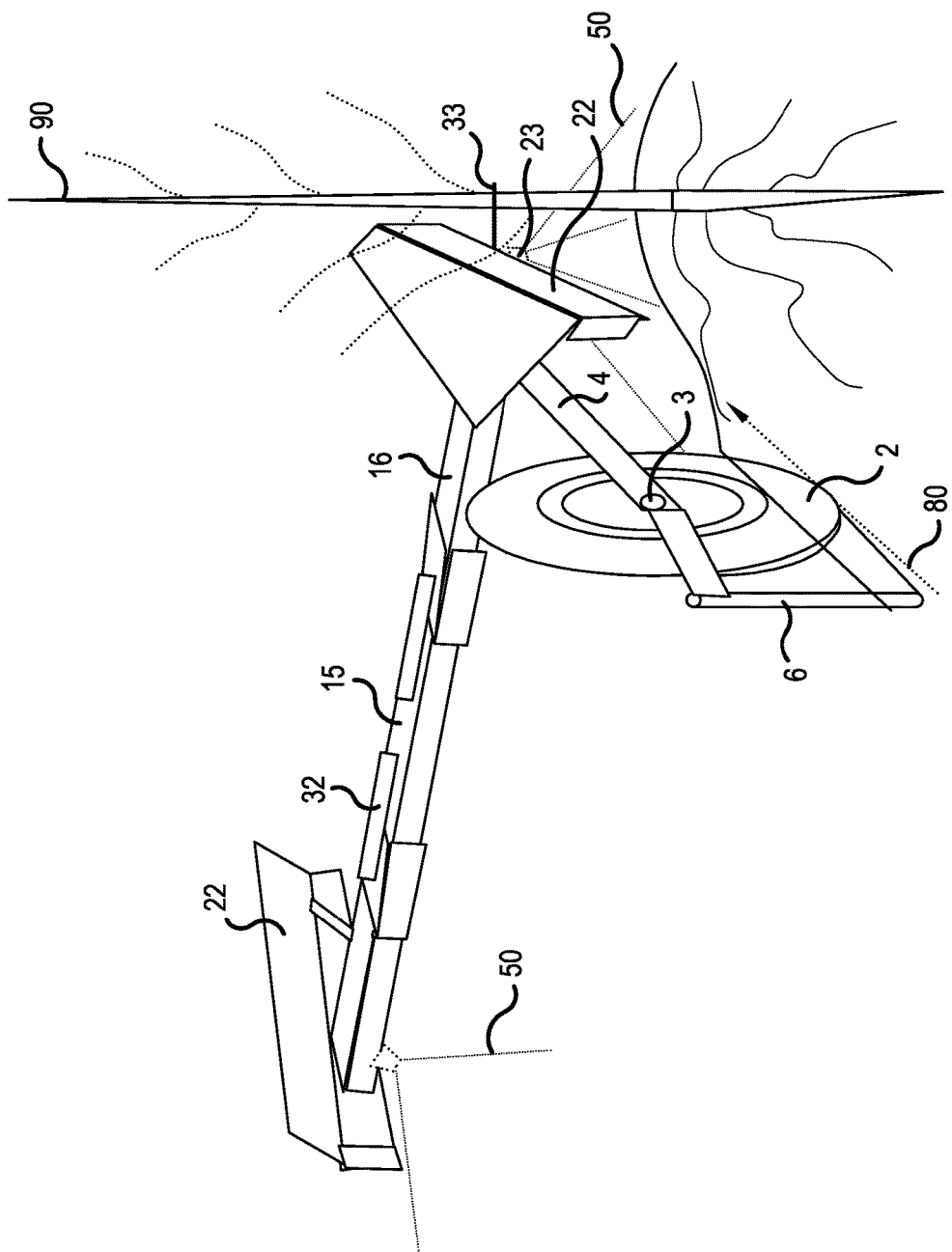
FIG. 2 is a rear perspective view of the applicator assembly of FIG. 1.
Figure 3:
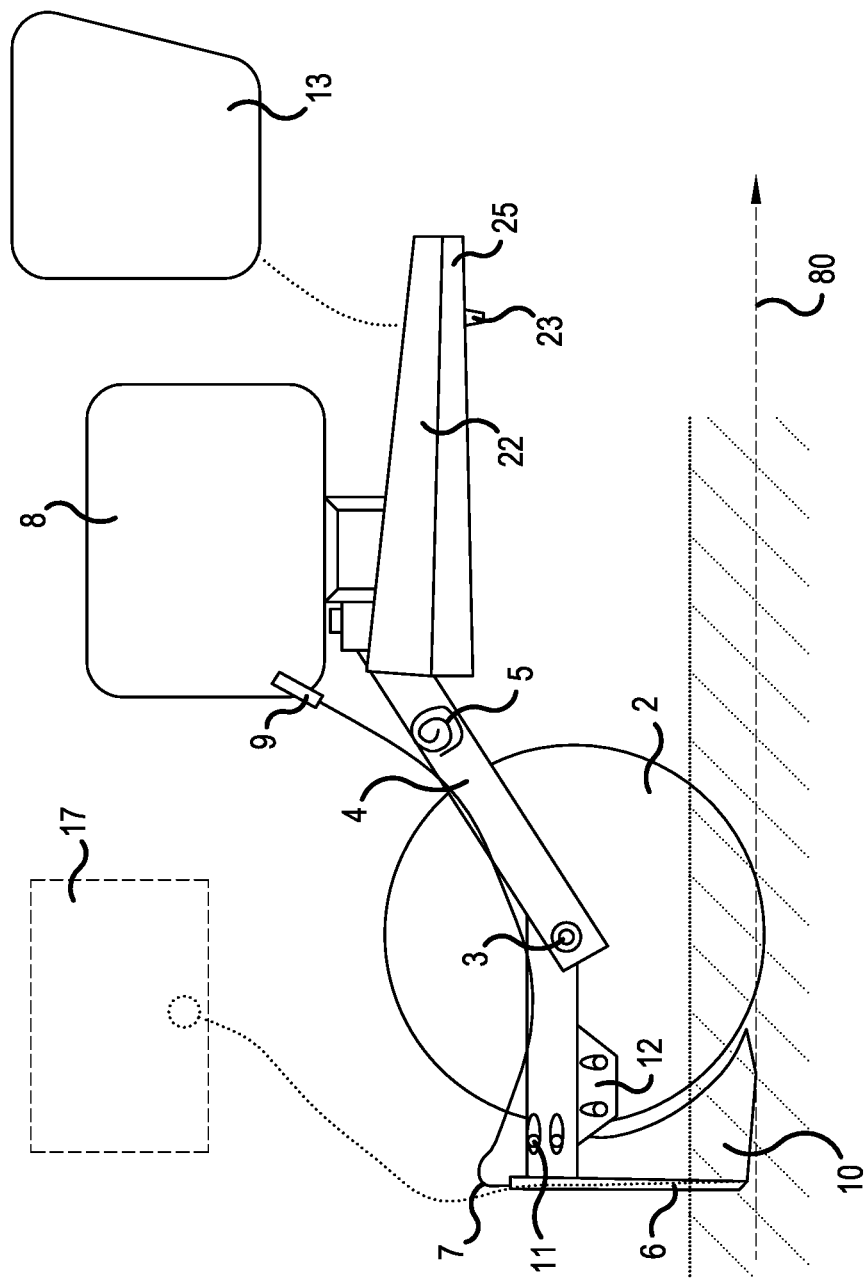
FIG. 3 is a side view of the applicator assembly of FIG. 1.

Referring to FIGS. 1 through 3, disclosed in a first embodiment is an applicator assembly 1 for applying an active substance to the root zone of a plurality of plants 90. Applicator assembly 1 comprises a cutting element or sharpened disk 2 which is connected by an axis 3 to a cutting element arm 4. The cutting element arm 4 is spring loaded at 5. The sharpened disk 2 rotates around axis 3 to generate an incision in the ground. An injector 6 is positioned so that it trails the sharpened disk 2 when the sharpened disk is moving forward to generate an incision in the ground. The injector 6 is connected by a flexible hose 7 to a spray tank 8 which contains the active substance. A switch 9 controls the application of the active substance either by manual or automatic switching responsive to a sensor.

The injector 6 includes a flat metal injector tine 10 which is shaped and positioned to run close to the sharpened disk 2. The injector 6 is adjustable by means of adjustment bolts 11 which change the position of the injector.

A mudflap 12 is positioned over the disk 2 to prevent mud from fouling the injector.

The applicator assembly includes a positioning device which is adapted to allow the position of the sharpened disk 2 and injector 6 to change such that an incision is generated in some material in the root zone while the sharpened disk 2 moves over other material in the root zone. The sharpened disk will therefore lift over heavy roots and rocks while incising lighter roots and soil.

The positioning device is in the form of a spring 5 which biases cutting element arm 4 and therefore the sharpened disk 2 and injector 6 with respect to the ground. The positioning device can bias the cutting element arm 4 downwardly or upwardly with respect to the ground, depending upon the requirements for the incision. Alternatively the positioning device can be in another form such as a hinge.

The applicator assembly 1 further includes a coupling in the form of tool bar 15 which connects the cutting element arm 4 with a vehicle 20. The tool bar 15 includes a shock absorber to allow lateral contraction from pressure on the arm in a lateral direction. The tool bar 15 is connected with a vehicle 20 and with two arm extensions 16 which are adjustable in relation to tool bar 15 to adjust the horizontal length of the tool bar 15 and the positioning of the applicator assembly.

The applicator assembly 1 further includes a deflector 22 which is adapted to push branches and leaves out of the way of the sharpened disk 2 as it creates its incision. A surface applicator 23 such as a spray nozzle or granule applicator is associated with deflector 22 and acts to apply a composition onto the surface of the ground. The composition is stored in secondary vessel 13 which is a tank or granule hopper. Surface applicator 23 is in fluid or granule communication with secondary vessel 13 such that a fluid or granule can move from the secondary vessel 13 to the surface applicator 23. It can be seen that this composition can either be the active substance which is being injected through injector 6 or a separate composition such as a herbicide for killing weeds or other beneficial compound. The deflector 22 acts to push branches and tree trunks out of the way to allow the composition applied 50 by surface applicator 23 to be applied close to the base of the stem on the surface of the ground.

The combination of surface applicator 23 and the injector 6 means that the applicator assembly can be used for the simultaneous application of substances to different parts of the plant.

The deflector 22 acts to keep the applicator assembly in a consistent position by pushing the branches and tree trunks out of the way allowing for application of the active substance in the optimum position.

The applicator assembly 1 further includes a sensor 25 which is adapted to detect a plant. This allows for discrete deposits of the active substance only where the plant is positioned.

In use, the applicator assembly is used to treat a plurality of plants. The applicator assembly generates an incision in a portion of the root zone of each of the plurality of plants and injects the active substance into that incision. The portion of the root zone of a single plant in which the incision is generated extends from the plant at an angle less than 180° so that only a portion of the root zone is incised. Simultaneously a composition is applied onto the surface of the ground proximal to each of the plurality of plants by the spray nozzle or granule applicator 23.

FIGS. 1 and 3 also depict an alternative vessel 17 which comprises a granule hopper or tank and is shown in phantom. The alternative vessel 17 is in fluid or granule communication with the injector 6 by means of flexible tubing or the like.

It can be seen that this method of creating an incision and injecting an active substance into the incision allows for application of the active substance sufficiently proximal to each of the plurality of plants for the composition to be taken up by the roots of the plant. Further, while the cutting element or disk creates an incision on a portion of the roots of the plant it does not incise all of the roots and thus does not destroy the plant. The incision is narrow enough that it does not require closing after the incision is made.

This applicator assembly can be used in rough or stony ground as exemplified by the soils in which large trees such as timber trees are grown. As the tool bar 15 or the applicator assembly 1 includes suspension to allow the disk 2 to lift over rocks or particularly stout roots, the applicator assembly can be used in soil which is rocky and contains heavy roots.

The active substance may be applied below the soil surface as a granule from a mounted hopper or mounted system or as a solution from a spray tank.

Figure 4:
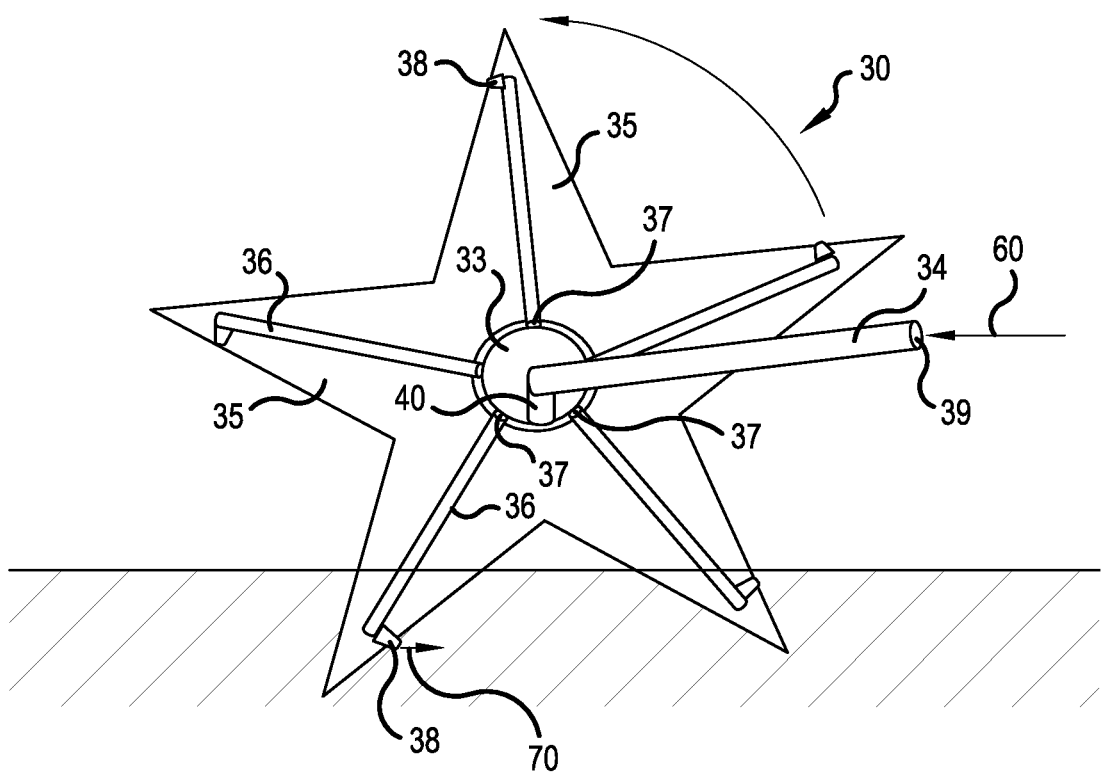
FIG. 4 is a side view of a spur in accordance with a second embodiment of the invention.

In a second embodiment, applicator assembly 1 comprises a spur 30 as best shown in FIG. 4. The spur 30 is connected at an axis 33 to a spur arm 34. Spur 30 comprises a plurality of spur tips 35 which are sharpened to allow the spur to generate multiple incisions in the root zone of the plurality of plants. Each spur tip 35 includes a spur conduit 36 extending down the spur tip 35 from a delivery position 37 near the axis 33 of the spur 30 to an application position 38 near the edge of the spur tip 35. The spur conduit 36 allows for the active composition 70 in the form of liquid or granules to move along the spur tip 35 and be applied into the incision made by the spur tip 35.

In this embodiment the active composition is delivered to the spur conduit 36 from a delivery conduit 39. The delivery conduit 39 is in fluid or granule communication 60 with an active composition tank or hopper (not illustrated in FIG. 4). Thus active composition is delivered to the delivery conduit 39 and moves along the delivery conduit 39. A connector 40 is positioned at the spur end of the delivery conduit 39.

In use as the spur 30 rotates about axis 33 each spur conduit 36 comes into position such that the connector 40 is in fluid communication with the spur conduit 36. At this point active substance is delivered from the delivery conduit 39 into the spur conduit 36 to allow for application of the active substance at the end of the spur tip 35.

Figure 5:
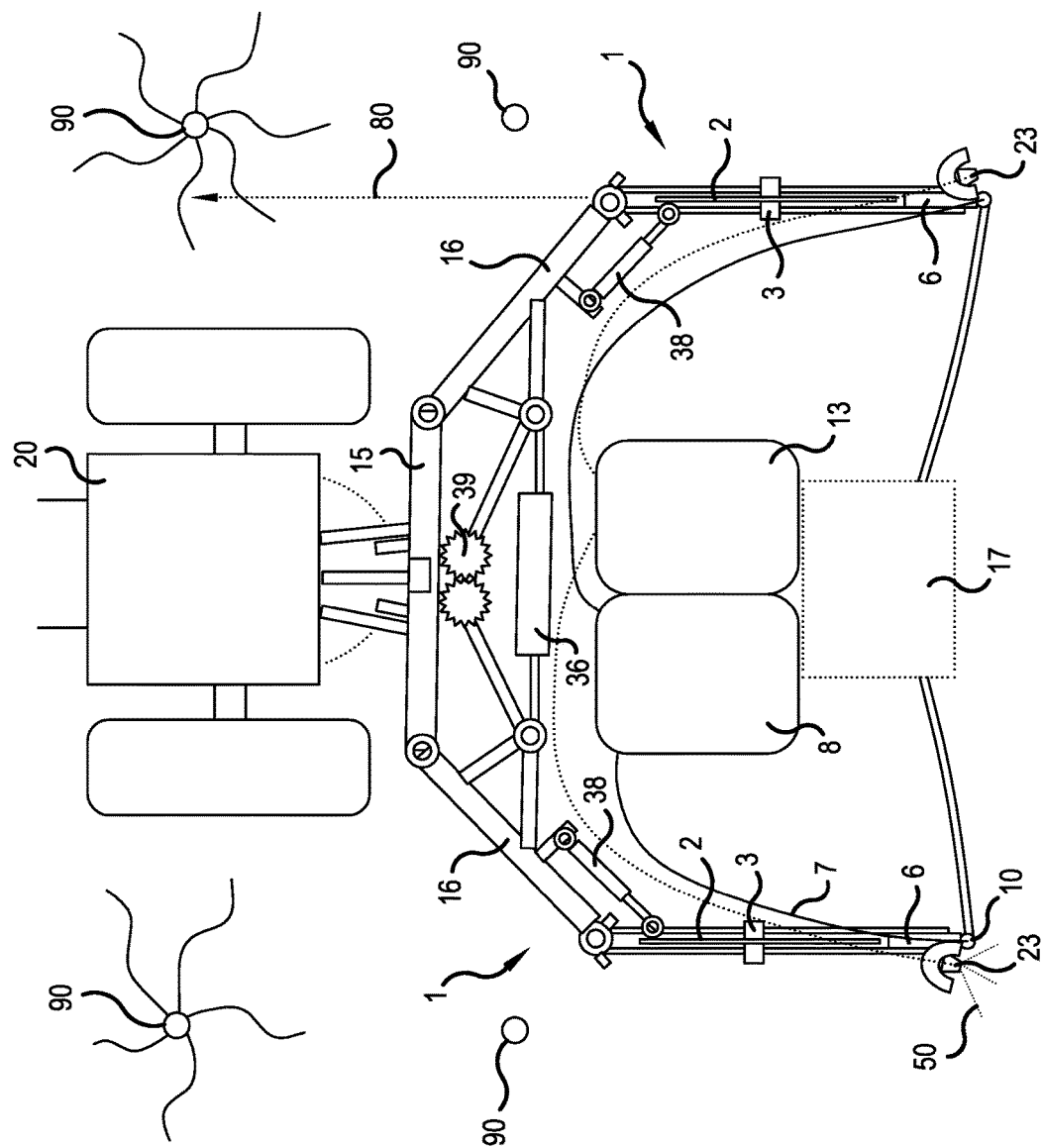
FIG. 5 is a top view of an applicator assembly in use on a vehicle in accordance with a third embodiment of the invention.

A third embodiment of the applicator assembly is shown in FIG. 5. Like numbers are used to refer to like features of the applicator assembly in this and the previous figures. Disclosed is an applicator assembly 1 for applying an active substance to the root zone of a plurality of plants. Applicator assembly 1 comprises a spur, cutting element or sharpened disk 2 which is connected by an axis 3 to a cutting element arm 4. The sharpened disk 2 rotates around axis 3 to generate an incision in the ground.

An injector 6 is positioned so that it trails the sharpened disk 2 when the sharpened disk 2 is moving forward to generate an incision in the ground. The injector 6 is connected by a flexible hose 7 to a spray tank 8 which contains the active substance. A switch 9 controls the application of the active substance either by manual or automatic switching responsive to a sensor.

The injector 6 includes a flat metal injector tine 10 which is shaped and positioned to run close to the sharpened disk 2. The injector 6 is adjustable by means of adjustment bolts 11 which change the position of the injector 6.

The applicator assembly includes a positioning device which is adapted to allow the position of the sharpened disk 2 and injector 6 to change such that an incision is generated in some material in the root zone while the sharpened disk 2 moves over other material in the root zone. The sharpened disk will therefore lift over heavy roots and rocks while incising lighter roots and soil.

The positioning device is in the form of a spring 5 which biases cutting element arm 4 and therefore the sharpened disk 2 and injector 6 with respect to the ground. The positioning device can bias the cutting element arm 4 downwardly or upwardly with respect to the ground, depending upon the requirements for the incision. Alternatively the positioning device can be in another form such as a hinge.

A mudflap 12 is positioned over the disk 2 to prevent mud from fouling the injector.

The applicator assembly 1 further includes a coupling in the form of tool bar 15 which connects the cutting element arm 14 with a vehicle 20. The tool bar 15 is hingedly connected to end sections 16 which are in turn connected to cutting element arms 4. End sections 16 can therefore be swung forward to align with the tool bar 15 or swung rearward to be positioned at an angle to the tool bar 15. The end sections 16 are swung hydraulically using ram 36. This allows for adjustment in the horizontal width of the applicator assembly 1 which is significant for use between trees. This allows for application to crops and trees which vary in inter-row spacing.

End sections 16 act as a deflector and are adapted to push branches and tree trunks out of the way of the sharpened disk 2 as it creates its incision. A spray nozzle or surface applicator 23 is associated with deflector 22 and acts to spray or apply a composition onto the surface of the ground. It can be seen that this composition can either be the active substance which is being injected through injector 6 or a separate composition such as a herbicide for killing weeds or pesticide or other critical composition. The end sections 16 act to push the branches out of the way to allow the composition applied by spray nozzle or surface applicator 23 to be applied close to the base of the stem or trunk on the surface of the ground.

The combination of the spray nozzle or surface applicator 23 and the injector 6 means that the applicator assembly can be used for the simultaneous application of substances to different parts of the plant.

The end sections 16 further act to keep the applicator assembly in a consistent position between the trees by pushing the branches out of the way allowing for application of the active substance in the optimum position.

Shock absorbers 38 are positioned to cooperate with the end sections 16 so that the cutting element 2 does not swing widely on lifting the applicator assembly 1 from the ground at the end of a row of trees or plants. Interlocking cogs 39 ensure that the end sections 16 move equally forward or back to maintain a consistent profile of the applicator assembly.

The applicator assembly 1 further includes a sensor 25 which is adapted to detect a plant. This allows for discrete deposits of the active substance only where the plant is positioned. In use, the applicator assembly 1 is used to treat a plurality of plants. The applicator assembly 1 generates an incision in a portion of the root zone of each of the plurality of plants and injects the active substance into that incision. The portion of the root zone of a single plant in which the incision is generated extends from the plant at an angle less than 180° so that only a portion of the root zone is incised. Simultaneously a composition is applied onto the surface of the ground proximal to each of the plurality of plants by the spray nozzle or applicator 23.

FIG. 5 also shows an alternative vessel 17 which comprises a granule hopper or tank and contains the active substance. If used, the alternative vessel 17 is in fluid or granule communication with the injector 6.

Figure 6:
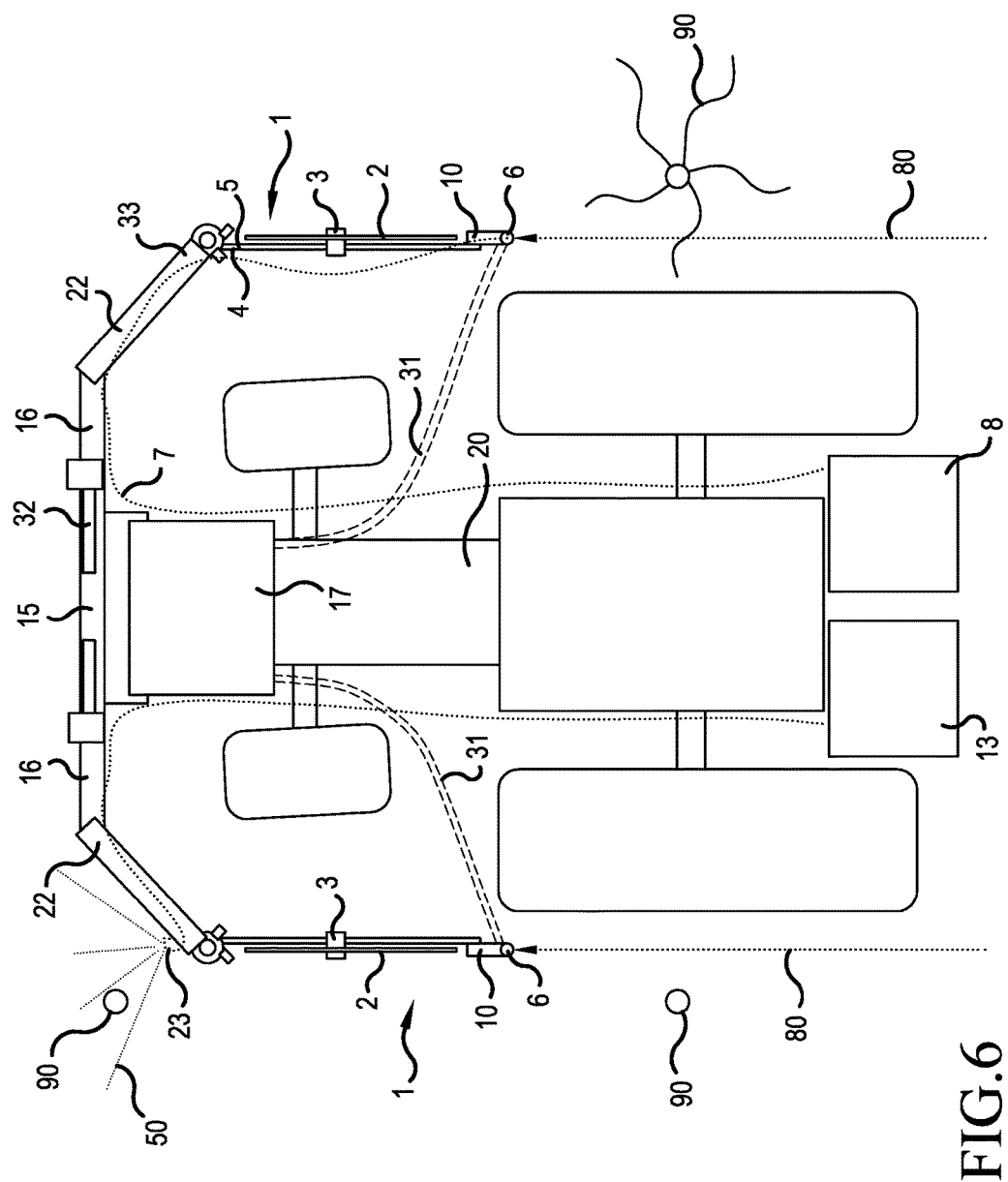
FIG. 6 is a top view of an applicator assembly in use on a vehicle in accordance with a fourth embodiment of the invention.

FIG. 6 shows a fourth embodiment of an applicator assembly 1 for applying an active substance to the root zone of a plurality of plants. As in the first embodiment, applicator assembly 1 comprises a cutting element or sharpened disk 2 which is connected by an axis 3 to a cutting element arm 4. The cutting element arm 4 is spring loaded at 5. The sharpened disk 2 rotates around axis 3 to generate an incision in the ground. An injector 6 is positioned so that it trails the sharpened disk 2 when the sharpened disk 2 is moving forward to generate an incision in the ground. The injector 6 is connected by a flexible hose 7 to a spray tank 8 which contains the active substance.

The injector 6 includes a flat metal injector tine 10 which is shaped and positioned to run close to the sharpened disk 2.

The applicator assembly includes a positioning device which is adapted to allow the position of the sharpened disk 2 and injector 6 to change such that an incision is generated in some material in the root zone while the sharpened disk 2 moves over other material in the root zone. The sharpened disk will therefore lift over heavy roots and rocks while incising lighter roots and soil.

The positioning device is in the form of a spring 5 which biases cutting element arm 4 and therefore the sharpened disk 2 and injector 6 with respect to the ground. The positioning device can bias the cutting element arm 4 downwardly or upwardly with respect to the ground, depending upon the requirements for the incision. Alternatively the positioning device can be in another form such as a hinge.

The applicator assembly 1 further includes a coupling in the form of a tool bar 15 which connects the cutting element arm 4 with the front of a vehicle 20. The tool bar 15 includes a shock absorber 32 to allow lateral contraction from pressure on the arm in a lateral direction. The tool bar 15 is connected with a vehicle 20 and with two arm extensions 16 which are adjustable in relation to central section 15 to adjust the horizontal length of the tool bar 15 and the positioning of the applicator assembly.

The applicator assembly 1 further includes a deflector 22 which is adapted to push branches and leaves out of the way of the sharpened disk 2 as it creates its incision.

A surface applicator 23 such as a spray nozzle or granule applicator is associated with deflector 22 and acts to apply a composition onto the surface of the ground. The composition is stored in secondary vessel 13 which is a tank or granule hopper. Surface applicator 23 is in fluid or granule communication with secondary vessel 13 such that a fluid or granule can move from the secondary vessel 13 to the surface applicator 23. It can be seen that this composition can either be the active substance which is being injected through injector 6 or a separate composition such as a herbicide for killing weeds or other beneficial compound. The deflector 22 acts to push branches and tree trunks out of the way to allow the composition applied by 23 to be applied close to the base of the stem on the surface of the ground.

The combination of surface applicator 23 and the injector 6 means that the applicator assembly can be used for the simultaneous application of substances to different parts of the plant.

The deflector 22 acts to keep the applicator assembly in a consistent position by pushing the branches and tree trunks out of the way allowing for application of the active substance in the optimum position.

The applicator assembly 1 further includes a sensor 25 which is adapted to detect a plant. This allows for discrete deposits of the active substance only where the plant is positioned. In use, the applicator assembly is used to treat a plurality of plants. The applicator assembly generates an incision in a portion of the root zone of each of the plurality of plants and injects the active substance into that incision. The portion of the root zone of a single plant in which the incision is generated extends from the plant at an angle less than 180° so that only a portion of the root zone is incised. Simultaneously a composition is applied onto the surface of the ground proximal to each of the plurality of plants by the spray nozzle or granule applicator 23.

FIG. 6 also depicts an alternative vessel 17 which comprises a granule hopper or tank and is shown in phantom. The alternative vessel 17 is in fluid or granule communication with the injector 6 by means of flexible tubing 31.

This applicator assembly can be used in rough or stony ground as exemplified by the soils in which large trees such as timber trees are grown. As the tool bar 15 or the applicator assembly 1 includes suspension to allow the disk 2 to lift over rocks or particularly stout roots, the applicator assembly can be used in soil which is rocky and contains heavy roots.

The active substance may be applied below the soil surface as a granule from a mounted hopper or mounted system or as a solution from a spray tank.

The applicator assembly can be used without the operator needing to turn around on the vehicle 20 to confirm correct operation.

It can be seen that in use in any form the applicator assembly allows for the application of a composition to a plurality of perennial plants at some speed. The operator is not required to make two separate applications of separate compositions. Further the operator is not required to bend or stop to move either low hanging branches or remove heavy roots and rocks from the path of the applicator assembly. This ensures that application is swifter than would otherwise be possible.

The active substance which is applied to perennial plants may, for example, be in the form of an emulsion, suspension, paste, powder, dust or granules. The applicator assembly 1 is adapted to apply the composition in various forms.

The composition may comprise two or more active substances, e.g. two different root systemic pesticides, or a root systemic pesticide and a fertilizer.

The composition may contain from 0.1 to 99% by weight of the active substance, for example, 10 to 80% by weight of the active substance, and one or more agriculturally acceptable excipients. The excipients may, for example, be solid or liquid carriers.

In one form, the composition is a controlled-release formulation formulated for releasing the active substance at a particular rate over a period of time. Such formulations are advantageous as they can be used to provide release of the active substance for an extended period of time without the need for a further application of the active substance. The controlled-release formulation might be, for example, a controlled-release formulation as disclosed in JP 2005/187462. Such a composition comprises solid nucleus particles, an agrochemical component-holding layer formed around the nucleus particles and containing the active substance, and a coating layer formed around the agrochemical component-holding layer and containing a polyurethane resin. Such a composition may be produced, by, for example, adding the active substance and a raw binder material with rolling the solid nucleus particles to form the agrochemical component-holding layer containing the active substance around the nucleus particles, and subsequently adding a raw polyurethane resin to form a coating containing the polyurethane resin around the agrochemical component-holding layer.

The active substance may be any substance that has a physiological effect on the perennial plants, or that has activity against a pest or disease of the perennial plants, and that is capable of being taken up by the roots of the perennial plants.

The active substance may, for example, be a fertilizer, plant growth regulator, pesticide (e.g. an insecticide or fungicide), or a herbicide.

In some embodiments, the active substance is a fertilizer. The fertilizer may, for example, be a nitrogenous fertilizer—such as urea, ammonium nitrate, ammonium sulphate or anhydrous ammonia: phosphorus and sulphur—such as superphosphate; potassium—such as potassium sulphate; a compound fertilizer—such as di-ammonium phosphate; a micronutrient or mineral supplement—such as boron, molybdenum or zinc.

In some embodiments, the active substance is a plant growth regulator such as gibberellins, cytokinins, auxins, abscisic acid, ethylene or aviglycine hydrochloride In some embodiments, the active substance is a root systemic pesticide. The root systemic pesticide may be any pesticide, e.g. an insecticide or fungicide, which can be taken up systemically by the roots of a plant.

There are numerous pesticides which act systemically in plants.

Examples of insecticides which act systemically include acetyl choline esterase inhibitors such as dimethoate; sodium channel modulators such as pyrethroids: chlorine channel activators such as avermectins; inhibitors of chitin biosynthesis such as benzoylureas; nicotinic acetylcholine receptor agonists/antagonists such as imidacloprid, acetamiprid, thiomethoxam, clothianidin, thiacloprid, nitenpyram or dinotefuran; anthranilic acid diamides such as chlorantraniliprole; and phthalic acid diamides such as flubendiamide.

Examples of fungicides which act systemically in plants include benzimadazoles such as benomyl; dicarboximides such as procymidone; demethylation inhibiting fungicides such as tebuconazole: phenylamides such as metalaxyl; and morpholines such as tridemorph.

The root systemic pesticide may, for example, be a root systemic insecticide selected from the following classes of insecticides: acetyl choline esterase inhibitors; sodium channel modulators; chlorine channel activators; inhibitors of chitin biosynthesis; nicotinic acetylcholine receptor agonists/antagonists, e.g. a neonicotinoid such as imidacloprid, acetamiprid, thiomethoxam, clothianidin, thiacloprid, nitenpyram or dinotefuran; anthranilic acid diamides: and phthalic acid diamides; or a root systemic fungicide selected from the following classes of fungicides: benzimadazoles: dicarboximides: demethylation-inhibiting fungicides; phenylamides; and morpholines.

When the root systemic pesticide is a nicotinic acetylcholine receptor agonist/antagonist, the root systemic pesticide may, for example, be imidacloprid, acetamiprid, thiomethoxam, clothianidin, thiacloprid, nitenpyram or dinotefuran. Preferred nicotinic acetylcholine receptor agonists/antagonists include imidacloprid, clothianidin and dinotefuran.

For some perennial crops it may be desirable to apply a herbicide to the plants, for example, it may be desirable to apply a defoliant or other herbicide to the plants shortly before harvesting the plants or a product of the plants. In some embodiments, the active substance is a herbicide. The herbicide may be a herbicide selected from the following classes of herbicides: inhibitors of acetolactate synthase—for example sulfonyl ureas; inhibitors of photosynthesis and photosystem II—for example triazines or disrupters of plant cell growth—for example pyridines.

The perennial plants may be any perennial plants grown in a row. By a "row of plants" or "plants grown in a row" it is meant plants grown in a line. The line may be straight or may be curved, for example, along the contours of the landscape.

The perennial plants may, for example, be fruit-bearing trees, for example, trees bearing stone fruit, pome fruit or soft fruit such as apples, pears, plums, peaches, almonds or cherries. The perennial plants may be nut-producing trees, for example, brazil nut, cashew nut or macadamia nut. The perennial plants may also be citrus fruit trees, such as orange, lemon, grapefruit or tangerine trees. The perennial plants may also be another perennial plant grown for commercial purposes such as olive trees, coconut trees or rubber trees.

The perennial plants may be trees grown for the production of wood, pulp, paper or timber. The perennial plants may be, for example, a plant of a *Albies* sp., *Eucalptus* sp., *Picea* sp., *Pinus* sp., *Aesculus* sp., *Platanus* sp., *Tilia* sp., *Acer* sp., *Tsuga* sp., *Fraxinus* sp., *Sorbus* sp., *Betula* sp., *CralAegus* sp., *Ulmus* sp., *Quercus* sp., *Salix* sp. or *Populus* sp. Such plants include the species of *Aescuhs: A. hippocastanum, A. pariflora, A. carnea*; the species of *Platmus: P. aceriflora, P. occidentalis, P. racemosa*; the species of *Picea: P. abies*; the species of *Pimus: P. radiate, P. ponderosa, P. contorta, P. sylvestre, P. elliottii. P. montecola. P. albicaulis, P. resinosa, P. palustris, P. taeda, P. flexilis, P. jefregi, P. baksiana, P. strobes*; and the species of *Eucaylptus: E. grandis, E. globulus, E. camadentis, E. nitens, E. obliqua, E. regnans, E. pilularus*.

In some embodiments, the perennial plants are *Acacia mangium, Khaya senegalensis, Araucaria cunninghamii, Araucaria bidwillii, Eucalyptus pilularis, Eucalyptus globulus, Eucalyptus agglomerate, Eucalyptus dunnii, Eucalyptus grandis, Eucalyptus cloezina, Eucalyptus regnans, Callitris intratropica, Corymbia citriodora, Pinus taeda, Pinus pinaster, Pinus caribaea* or *Pinus elliottii*.

The perennial plants can include temperate, sub tropical and tropical species. The plants may be plants of any age. For example, the plants may be between a few months old and 101 years of age. In some embodiments, the plants are more than 1 year of age. In some embodiments, the plants are more than 2 years of age.

The active substance is applied below the soil surface sufficiently proximate to the perennial plants in the row for the active substance to be taken up by the roots of the plants. A person skilled in horticulture or forestry could readily determine, having regard to the type of the plants and the age of the plants, an appropriate distance from the perennial plants for the active substance to be applied at a position where the active substance will be taken up by the feeder roots of the plants.

As will be apparent to a person skilled in the art, applying an active substance below the soil surface sufficiently proximate to a row of perennial plants for the active substance to be taken up by the roots of the plants will typically result in some damage to the roots of the plants. Root damage can be minimised by reducing the depth of application, increasing the distance of application from the plants, or by applying the active substance along only one side of the row of plants. A person skilled in horticulture or forestry would readily be able to determine an appropriate depth and distance from the stems of the plants to minimise root damage and achieve uptake of the substance by the roots of the plant.

The active substance is typically applied below the soil surface at a distance of about 10 cm to 2 meters, e.g. 10 cm to 80 cm, from the base of the stem of the plants in the row. In some embodiments, the active substance is applied below the soil surface at a distance of about 20 to 40 cm from the base of the stem of the plants. The active substance is typically applied at a depth of 2 to 50 cm, e.g. 2 to 30 cm, below the soil surface. In some embodiments, the active substance is applied at a depth of 10 to 15 cm below the soil surface.

The active substance may be applied below the soil surface as the pure compound. However, more typically. the active substance is applied in the form of a composition comprising the active substance together with excipients customarily used in agricultural formulations.

The composition comprising the active substance may, for example, be in the form of an emulsion, suspension, paste, powder, dust or granules. The composition may comprise two or more active substances, e.g. two different root systemic pesticides, or a root systemic pesticide and a fertilizer.

The composition may contain from 0.1 to 99% by weight of the active substance, for example, 10 to 80% by weight of the active substance, and one or more agriculturally acceptable excipients. The excipients may, for example, be solid or liquid carriers.

The compositions may be prepared by methods for preparing agricultural formulations known in the art.

In some embodiments, the active substance is applied in a continuous line. In other embodiments. the active substance is applied as a series of deposits. The series of deposits typically forms a discontinuous line along the row of perennial plants. The series of deposits may be in a single line or the various deposits may be offset from one or more of the preceding deposits. For example, the deposits may form a discontinuous line along the row of perennial plants as follows:

. . . . . . . . . . . . . . . . . . or

_____ or

- _ - _ - _ - _ - _ - or

= = = = = = = = = = = = = = = = = = = = = = or

/// /// /// /// /// /// ///

As the active substance is applied below the soil surface sufficiently proximate to the perennial plants for the substance to be taken up by the roots of the plants, typically, a relatively small amount of a composition comprising the active substance is required for each perennial plant. Typically, the volume of the composition applied for each plant is less than the volume of a composition comprising the same active substance that would be applied if the active substance were applied by spraying or drenching. Accordingly, considerable cost savings can be achieved by applying the active substance by the method of the present invention.

As discussed above, when the active substance is a root systemic pesticide, the method of present invention may be used to control a pest on a row of perennial plants. As used herein, a reference to the "control" of a pest on a row of perennial plants encompasses preventing pests from infesting or damaging plants in the row as well as combating an existing infestation of a pest on one or more of the plants in the row. The pest may be any organism, e.g. an insect or other invertebrate or a fungus, which has an adverse effect on the growth or health of the plants.

The method of the present invention may be used to control any pests against which the root systemic pesticide is active. For example, when the root systemic pesticide is a neonicotinoid, the method may be used to control *Coleoptera* sp. (beetles), *Hemiptera* sp. (tree bugs), *Homoptera* sp. (e.g. aphids, mealy bugs and scales) or *Hymenopetra* sp. (e.g. wasps, ants and sawflys) on the perennial plants. When the root systemic pesticide is an anthranilic acid diamine such a chlorantraniprole, the method may be used to control Lepidoptera pests.

When the active substance is a root systemic pesticide, the root systemic pesticide is applied below the soil surface in an amount effective to control the pest on the perennial plants. The effective amount will vary depending on factors such as the particular root systemic pesticide used, the particular formulation used, the depth and distance from the plant stems at which the pesticide is applied, the particular pest, and the age and species of the perennial plants. It is well within the skill of a person skilled in the horticultural or forestry field to determine an effective amount of a root systemic pesticide to control a pest on a row of perennial plants having regard to the disclosure of this specification. The root systemic pesticide is typically applied at a rate of about 0.2 to 5 grams of root systemic pesticide for each plant.

Example

Near Casino, northern New South Wales, Australia in the 2006-2007 season, chlothianidin as a suspension (200 g/L) in water at 0.5, 1.0 and 1.5 grams of active ingredient per tree (gai/tree) was applied to 2 year old *Eucalyptus dunni* trees for the control of psyllids *Creiis lituratus* during winter and chrysomelid leaf beetles during summer.

A single application below the soil surface was made by coulter 20-40 cm from the base of the stem of the trees and to a depth of 10-15 cm in 128 L of water per hectare. Psyllid lerp counts were taken 141 and 303 DAT (days after treatment). Tree height was measured at treatment and then at 303 DAT. Diameter at breast height was measured at 303 DAT.

The sub-surface application of clothianidin at 0.5 to 1.5 gai/tree significantly reduced psyllid lerp counts and improved the growth of *E. dunni* under high psyllid pressure up to 303 DAT.

Increase in wood volume at 1 gai/tree for 303 DAT was 8.5 m$^3$/ha.

TABLE 1

Comparison of three rates of Clothianidin applied by subsurface application for the control of psyllids

| | | Mean lerp count per 5 terminal leaflets | |
|---|---|---|---|
| Treatment | Rate gai/tree | Oct. 7, 2006 (141 DAT)* | Mar. 19, 2007 (303 DAT)* |
| 1. Untreated control | Nil | 3.56 a | 16.73 A |
| 3. Clothianidin | 0.5 | 2.33 b | 3.50 B |
| 4. Clothianidin | 1 | 0.71 c | 2.06 B |
| 5. Clothianidin | 1.5 | 0.58 c | 0.69 B |
| P value | | 0.0000 | 0.0000 |
| LSD (5% level)** | | 1.13 | 3.57 |

*Means within columns followed by the same letter are not significantly different at the 5% level
**Means least significant difference at the 5% level

TABLE 2

Comparison of three rates of Clothianidin for the effect of psyllid control on growth of *E. dunni*

| Treatment | Rate gai/tree | Mean tree height (cm)* 303 DAT | Mean increase in tree height (cm)* 0-303 DAT | DBM+ (cm) 303 DAT |
|---|---|---|---|---|
| 1. Untreated control | nil | 447 cd | 159 bc | 5.03 c |
| 3. Clothianidin | 0.5 | 500 bc | 198 ab | 5.44 bc |
| 4. Clothianidin | 1 | 526 b | 228 a | 5.91 ab |
| 5. Clothianidin | 1.5 | 594 a | 229 a | 6.67 a |
| P value | | 0.000 | 0.0002 | 0.0024 |
| LSD (5% level) | | 62.86 | 49.84 | 8.74 |

+DBM = diameter at breast height (1.3 m above ground level)

Effect on Wood Volume

The difference in volume between the untreated and the 1 gai/tree treatment can be calculated over 303 days

| Rate | Mean tree height (m) | Mean tree diameter (cm) | Mean wood vol/ha (m$^3$) |
|---|---|---|---|
| Untreated control | 4.47 | 5.03 | 13.7 |
| 1 gai/tree | 5.26 | 5.91 | 22.2 |

The invention claimed is:

1. An applicator assembly for applying a substance selected from the group consisting of fertilizer, plant growth regulator, insecticide, fungicide and herbicide to a root zone of a plurality of plants, the applicator assembly comprising:
   a subsoil applicator, the subsoil applicator comprising a cutting element for generating an incision in a ground surface, and an injector associated with the cutting element to allow the substance to be injected into the incision;

a surface applicator positioned to apply a composition proximal to a base of a stem or trunk on the surface of the ground;

a deflector adapted to push branches or leaves or tree trunks for a path of the cutting element and for a path of the surface applicator; and the surface applicator being located on the deflector.

2. An applicator assembly as defined in claim 1, wherein the composition is a herbicide.

3. An applicator assembly as defined in claim 1, wherein the composition is the same as the active substance.

4. An applicator assembly as defined in claim 1, wherein the plurality of plants is positioned in a row.

5. An applicator assembly as defined in claim 1, adapted to deliver the substance selected from the group consisting of fertilizer, plant growth regulator, insecticide, fungicide and herbicide at a soil depth of 2-30 cm.

6. An applicator assembly as defined in claim 1, wherein the injector is adapted to deliver a continuous application of active substance.

7. A method of treating a plurality of plants using the applicator assembly as defined in claim 1, the method comprising:

i) using an assembly to generate an incision in a portion of a root zone of the plurality of plants;

ii) using the assembly to inject a substance selected from the group consisting of fertilizer, plant growth regulator, insecticide, fungicide and herbicide into the incision;

iii) using the assembly to move branches aside, and iv) applying a composition to a surface of ground adjacent the plurality of plants.

8. A method of treating a plurality of plants as defined in claim 7, wherein the portion of the root zone of a single plant in which the incision is generated extends from the single plant at an angle of less than 180 degrees.

9. A method of treating a plurality of plants as defined in claim 8, wherein the incision extends through soil and roots that the cutting element can make an incision in but skips over rocks and roots that the cutting element cannot make an incision in.

10. A method of treating a plurality of plants as defined in claim 7, wherein the incision extends through soil and roots that the cutting element can make an incision in but skips over rocks and roots that the cutting element cannot make an incision in.

11. A method of treating a plurality of plants as defined in claim 7, wherein the incision is generated by a cutting element.

12. A method of treating a plurality of plants as defined in claim 7, wherein the injection is performed by an injector associated with a cutting element.

13. A method of treating a plurality of plants as defined in claim 7, wherein the composition is a herbicide.

14. A method of treating a plurality of plants as defined in claim 7, wherein the plurality of plants are positioned in a row.

15. A method of treating a plurality of plants as defined in claim 7, wherein the plurality of plants that are treated are in forest plantations.

16. A method of treating a plurality of plants as defined in claim 7, wherein the method of treatment is performed by a vehicle mounted applicator assembly that travels at average speeds of over 4 km/hr.

17. An applicator assembly as defined in claim 1, further comprising a sensor to detect a plant.

\* \* \* \* \*